United States Patent

Rakhit

[11] 4,003,995
[45] Jan. 18, 1977

[54] GLYCOSYL ESTERS OF PHENOXYISOBUTYRIC ACIDS

[75] Inventor: Sumanas Rakhit, Dollard des Ormeaux, Canada

[73] Assignee: American Home Products Corporation, New York, N.Y.

[22] Filed: Jan. 2, 1976

[21] Appl. No.: 646,210

[52] U.S. Cl. .............................. 424/180; 536/119
[51] Int. Cl.² ....................................... A61K 31/70
[58] Field of Search ............... 260/234 R, 210 AB; 424/180

[56] References Cited

UNITED STATES PATENTS 3,723,617    3/1973    Sutton .............................. 424/180

OTHER PUBLICATIONS

Wagner and Zook, Synthetic Org. Chem., Wiley & Sons, N.Y. 1953, p. 484 paragraph 290.

Primary Examiner—Lewis Gotts
Assistant Examiner—Cary Owens
Attorney, Agent, or Firm—Stephen Venetianer

[57] ABSTRACT

Glycosyl esters of formula

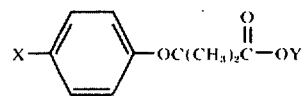

in which X is chloro, bromo, or lower alkyl and Y is tetra-(lower alkanoyl) or tetrabenzoyl β-D-glucosyl or tri(lower alkanoyl) or tribenzoyl β-D-ribosyl are disclosed. These esters possess antihyperlipoproteinemic activity. Methods for preparation and use, as well as pharmaceutical compositions of the glycosyl esters, also are disclosed.

6 Claims, No Drawings

GLYCOSYL ESTERS OF PHENOXYISOBUTYRIC ACIDS

BACKGROUND OF THE INVENTION a. Field of the Invention

This invention relates to glycosyl esters of phenoxyisobutyric acid having valuable pharmaceutical properties, to a process for preparing the esters, to pharmaceutical preparations thereof, and to a method for their use.

b. Prior Art

The association of excessive plasma concentrations of lipoprotein or of plasma lipids with increased risk of heart attack, stroke, and sudden death is well established. Consequently, the consensus of informed opinion is that elevated levels of cholesterol and/or triglycerides should be reduced by appropriate long term therapy.

The generally accepted Frederickson-Levy-Lees classification of lipid disorders based on lipoprotein disturbances lists five categories, Types I to V, of hyperlipoproteinemia. This classification allows a more rational choice of therapeutic programs for the treatment of hyperlipoproteinemia, see R. I. Levy, Fed. Proc., 30, 829 (1971). Although a variety of drugs are available for the treatment of hyperlipoproteinemia, none of them is adequate for the general treatment of all types of hyperlipoproteinemias. At the present time, the preferred drugs for treating hyperlipoproteinemia are dependent on the classification of the syndrome and are thus specific for each syndrome; for example, see R. S. Lees and D. E. Wilson, New Engl. J. Med., 284, 186 (1971).

The glycosyl esters of this invention are prepared by a convenient process from readily available starting materials. Consequently, the esters are inexpensive and readily available.

The esters of this invention feature a combination of chemical subunits; namely, a acylal ester, comprising a glycosyl moiety, associated with a phenoxyisobutyric acid. Esters of phenoxyisobutyric are known; for example, lower alkyl esters thereof are described in U.S. Pat. No. 3,262,850, issued July 26, 1966 and 3-pyridylmethyl esters thereof are described in U.S. Pat. No. 3,369,025, issued February 13, 1968. Other prior art compounds include derivatives of 2-nicotinamido-1-O-nicotinoyl-β-D-glucose, German Offenlegengschrift 2501861, published Jan. 25, 1974. Prior Art compounds are distinguished from the present invention in that they lack the novel ester moiety of the compounds of this invention.

SUMMARY OF THE INVENTION

The glycosyl esters of this invention are represented by formula 1.

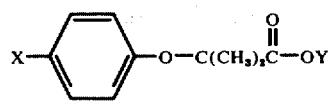

in which X is chloro, bromo or lower alkyl and Y is

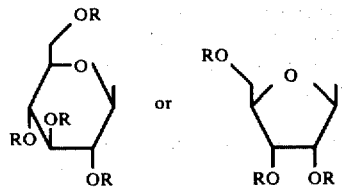

wherein R is lower alkanoyl or benzoyl. The latter two formulae represent teta(lower alkanoyl) or tetrabenzoyl β-D-glycosyl and tri(lower alkanoyl) or tribenzoyl β-D-ribosyl, respectively.

The esters are readily prepared by a process described herein.

Another aspect of the invention relates to pharmaceutical formulations comprising the glycosyl esters of formula 1 and a pharmaceutically acceptable carrier.

The compounds of formula 1 possess hypocholesterolemic and triglyceride lowering properties and administration of the compounds to hyperlipoproteinemic mammals lowers blood cholesterol and triglyceride concentrations.

DETAILS OF THE INVENTION

The term "hyperlipoproteinemia" as used herein contemplates an increase over normal levels in one or more of the plasma lipoprotein classes and includes conditions wherein the levels of plasma cholesterol, triglycerides or both are increased.

The term "lower alkyl" as used herein contemplates hydrocarbon radicals having one to three carbon atoms and includes methyl, ethyl, isopropyl and propyl.

The term "lower alkanoyl" as used herein contemplates straight and branched chain alkanoyl radicals containing from two to six carbon atoms and includes acetyl, propionyl and hexanoyl.

The hypocholesterolemic and triglyceride lowering properties of the compounds of formula 1 of the present invention are demonstrated in standard pharmacologic tests, for example, in procedures similar to the in vivo tests, described by C. H. Duncan and M. M. Best, Amer. J. Clin, Nutr., 10, 297 (1962), and by the general tests described by L .W. Kinsell in "Pharmacologic Techniques in Drug Evaluation," Vol. 2, P. .E. Siegler and J. H. Moyer, Eds., Year Book Medical Publishers, Inc., Chicago, 1967, pp. 711 – 720.

When used as antihyperlipoproteinemic agents, a blood cholesterol and triglyceride lowering amount of the compounds of formula 1 is administered to hyperlipoproteinemic mammals, for example rats, either alone or with pharmaceutically acceptable carriers, the proportion of such carriers being determined by the solubility and chemical nature of the compound, chosen route of administration and standard biological practice. For example, the compounds may be administered orally in solid form containing such excipients as starch, milk sugar, certain types of clay and so forth. They may also be administered orally in the form of solutions or they may be injected parenterally. For parenteral administration they may be used in the form of a sterile solution containing other solutes, for example, enough saline or glucose to make the solution isotonic.

The dosage of the present esters of formula 1 will vary with the form of administration and the particular compound chosen. Furthermore, it will vary with the particular host under treatment. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects and preferably at a level that is in a range of from about 0.1 mg to about 100 mg per kilo per day, although as aforementioned variations will occur. However, a dosage level that is in the range of from about 1.0 mg to about 50 mg per kilo per day is most desirably employed in order to achieve effective results.

Process

A convenient process for preparing the compounds of formula 1 comprises reacting a phenoxyisobutyric acid addition salt of formula 2

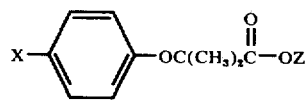

in which X is as defined herein and Z is a metal selected from the group consisting of sodium, potassium, lithium or silver salt with 0.8 to 2.0 moles preferably 1.0 mole, of a compound selected from the group consisting of the compounds of formulae 3a and 3b

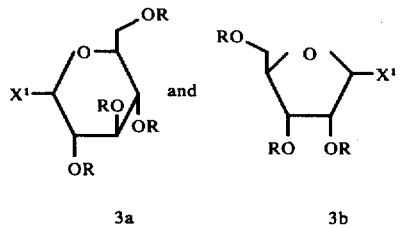

in which $X^1$ is chloro or bromo and R is as defined herein, to give the corresponding compound of formula 1. Generically these compounds are known as tetra(-lower alkanoyl) or tetrabenzoyl 1α-chloro- or 1α-bromo-D-glucose in the case of the compound represented by formula 3a and tri(lower alkanoyl) or tribenzoyl 1α-chloro- or 1α-bromo-D-ribose in the case of the compound represented by formula 3b.

The reaction is performed preferably in a polar, aprotic solvent. Examples of suitable solvents include dimethylformamide, dimethyl acetamide, acetonitrile, acetone, hexamethylenetriphosphoramide, tetrahydrofuran and dioxane. Temperatures for the reaction range from 50° to 150° C, preferably 55° to 125° C. The time required to effect the reaction is dependent on the temperature; however, a reaction time ranging from one to 24 hours, or more often 2 to 6 hours, usually is sufficient.

Alternatively, the compounds of formula 1 are prepared by reacting a phenoxyisobutyric acid of formula 2 in which X is as defined herein and Z is hydrogen according to the aforementioned conditions in the presence of an excess, preferably 1.0 to 2.0 equivalents, of a suitable base, for example, sodium or potassium carbonate or sodium hydride. Preferred conditions include the use of acetone as the solvent and sodium or potassium carbonate as the base.

The requisite phenoxyisobutyric acids and their addition salts of formula 2 are either known, U.S. Pat. No. 3,558,640, cited above, or are prepared by known methods.

With reference to the requisite compounds of formula 3a, 2,3,4,6-tetraacetyl-1α-bromo-D-glucose has been described by R. U. Lemieux, Methods in Carbohydrate Chemistry, Vol. 2, P. 221, Editors R. L. Whistler and M. L. Wolfrom, Academic Press Inc., New York and London, 1963.

With reference to the requisite compound of formula 3b, 2,3,5-triaacetyl-1α-bromo-D-ribose has been described by N. Yung and T. J. Fox in Methods in Carbohydrate Chemistry, Vol. 2, P. 109, Editors R. L. Whistler and M. L. Wolfrom, Academic Press, New York and London, 1963.

The following example illustrates further this invention.

EXAMPLE 1

2-(4-Chlorophenoxy)-2-methylpropionic acid 2,3,4,6-tetraacetyl-β-D-glucose-1-yl-ester Procedure:

A mixture of 236 mg (1.0 mmole) of the sodium salt of 2-(4-chlorophenoxy)-2-methylpropionic acid (the compound of formula 2 in which X is chloro and Z is sodium) and 411 mg (1.0 mmole) of 2,3,4,6-tetraacetyl-1α-bromo-D-glucose in 10 ml of dimethylformamide is heated at 120° C for a period of 2 hours. The mixture is cooled and poured into ice water. The resulting precipitate is collected and washed with water and dried. The precipitate is dissolved in methanol and the brown solution is treated with activated charcoal and filtered. The filtrate was evaporated to give the product in crystalline form, mp 130°–131°.

The title compound is also obtained by following the above described procedure but replacing acetobromo glucose with acetochloro glucose.

By following the above mentioned procedure, but replacing the sodium salt of 2-(4-chlorophenoxy)-2-methylpropionic acid with the sodium potassium, lithium or silver salt of 2-(4-bromophenoxy)-2-methylpropionic acid or the sodium, potassium, lithium or silver salt of 2-[4-(lower alkyl)-phenoxy]-2-methylpropionic acid, 2-(4-bromophenoxy)-2-meth propionic acid 2,3,4,6-tetraacetyl-β-D-glucose-1-yl ester and 2-[4-(lower alkyl)-phenoxy]-2-methylpropionic acid 2,3,4,6-tetraacetyl-β-D-glucose-1-yl ester are obtained, respectively.

By following the procedure of this example and using an appropriate compound of formula 2 but replacing 2,3,4,6-tetraacetyl-1α-bromo-D-glucose with 2,3,5-triacetyl-1α-bromo-D-ribose, the corresponding compound of formula in which Y is

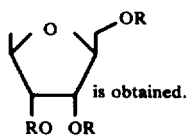

is obtained.

We claim:
1. A compound of formula 1

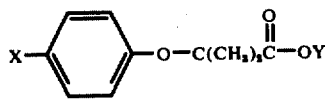

in which X is chloro, bromo or lower alkyl and Y is

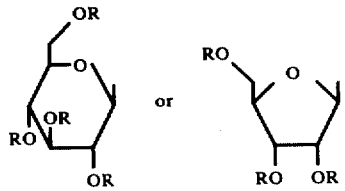

wherein R is lower alkanoyl or benzoyl.

2. 2-(4-chlorophenoxy)-2-methylpropionic acid 2,3,4,6-tetracetyl-β-D-glucose-1-yl ester as claimed in claim 1.

3. A method for lowering concentration of blood cholesterol and triglycerides in mammals which comprises administering orally or parentally to said mammal a blood cholesterol and triglyceride lowering amount of compound of formula 1 as claimed in claim 1.

4. The method of claim 3 in which the compound of formula 1 is 2-(4-chlorophenoxy)-2-methylpropionic acid 2,3,4,6-tetraacetyl-β-D-glucose-1-yl ester.

5. A pharmaceutical composition comprising a compound of formula 1 as claimed in claim 1 and a pharmaceutically acceptable carrier.

6. The pharmaceutical composition of claim 5 in which the compound of formula 1 is 2-(4-chlorophenoxy)-2-methylpropionic acid 2,3,4,6-tetraacetyl-β-D-glucose-1-yl ester.

* * * * *